United States Patent
Lee et al.

(10) Patent No.: US 9,707,340 B2
(45) Date of Patent: Jul. 18, 2017

(54) FLOW CONTROL LINE MANAGEMENT APPARATUS

(75) Inventors: Chaoyoung Lee, Weston, MA (US); Mei Zhang, Sharon, MA (US)

(73) Assignee: ZYNO MEDICAL LLC, Natick, MA (US)

( * ) Notice: Subject to any disclaimer, the term of this patent is extended or adjusted under 35 U.S.C. 154(b) by 514 days.

(21) Appl. No.: 13/460,071

(22) Filed: Apr. 30, 2012

(65) Prior Publication Data

US 2012/0283630 A1    Nov. 8, 2012

Related U.S. Application Data

(60) Provisional application No. 61/483,321, filed on May 6, 2011.

(51) Int. Cl.
*A61M 5/168*    (2006.01)

(52) U.S. Cl.
CPC .... *A61M 5/16827* (2013.01); *A61M 5/16881* (2013.01); *A61M 5/16886* (2013.01); *A61M 5/1689* (2013.01); *A61M 5/16813* (2013.01)

(58) Field of Classification Search
CPC .......... A61M 5/16813; A61M 5/16827; A61M 5/16881; A61M 5/16886
USPC ................. 604/65, 80, 81, 250, 251, 253
See application file for complete search history.

(56) References Cited

U.S. PATENT DOCUMENTS

| | | | | |
|---|---|---|---|---|
| 4,043,332 A | * | 8/1977 | Metcalf | A61M 5/1483 |
| | | | | 128/DIG. 12 |
| 4,094,318 A | * | 6/1978 | Burke | A61M 5/1689 |
| | | | | 128/DIG. 13 |
| 4,512,764 A | | 4/1985 | Wunsch | |
| 4,513,796 A | * | 4/1985 | Miller | A61J 3/002 |
| | | | | 141/100 |
| 4,559,036 A | | 12/1985 | Wunsch | |
| 4,637,817 A | | 1/1987 | Archibald et al. | |
| 4,673,389 A | * | 6/1987 | Archibald et al. | 604/81 |
| 4,681,563 A | * | 7/1987 | Deckert | A61M 5/1689 |
| | | | | 128/DIG. 13 |
| 4,714,463 A | * | 12/1987 | Archibald | A61M 5/16827 |
| | | | | 251/9 |
| 4,925,444 A | | 5/1990 | Orkin et al. | |
| 4,966,579 A | * | 10/1990 | Polaschegg | A61M 5/16831 |
| | | | | 604/131 |
| 5,032,112 A | * | 7/1991 | Fairchild | A61M 5/16831 |
| | | | | 604/123 |
| 5,059,173 A | * | 10/1991 | Sacco | 604/80 |
| 5,318,546 A | * | 6/1994 | Bierman | A61M 39/284 |
| | | | | 128/898 |
| 5,429,485 A | * | 7/1995 | Dodge | 417/442 |
| 5,693,232 A | * | 12/1997 | Brown | B01D 21/34 |
| | | | | 210/739 |
| 6,017,318 A | * | 1/2000 | Gauthier et al. | 600/578 |

(Continued)

*Primary Examiner* — Kevin C Sirmons
*Assistant Examiner* — Shefali Patel
(74) *Attorney, Agent, or Firm* — Boyle Fredrickson, S.C.

(57) ABSTRACT

A line management apparatus for managing multiple IV lines connected in a Y fitting provides for flow sensing and for electronic control of flow in the multiple lines. The line management apparatus may be used independently as a precise gravity feed IV system or may provide for use in combination with an infusion pump to ensure proper delivery of multiple solutions without blending of the multiple solutions.

17 Claims, 4 Drawing Sheets

(56) References Cited

U.S. PATENT DOCUMENTS

| | | | |
|---|---|---|---|
| 7,802,569 B2* | 9/2010 | Yeates | A61M 15/0086 |
| | | | 128/200.14 |
| 8,382,711 B2* | 2/2013 | Dudar et al. | 604/123 |
| 2003/0212381 A1* | 11/2003 | Whitehead, III | 604/514 |
| 2005/0119626 A1* | 6/2005 | Rahe-Meyer | A61M 5/16881 |
| | | | 604/250 |
| 2012/0029449 A1* | 2/2012 | Khosrowshahi | A61F 13/02 |
| | | | 604/321 |

* cited by examiner

FLOW CONTROL LINE MANAGEMENT APPARATUS

CROSS-REFERENCE TO RELATED APPLICATIONS

This application claims the benefit of U.S. provisional application 61/483,321 filed May 6, 2011 entitled "Infusion Line Management Apparatus and Method" hereby incorporated by reference in its entirety.

BACKGROUND OF THE INVENTION

The present invention relates to systems for intravenous (IV) administration of drugs and in particular to a system allowing the delivery of multiple IV solutions to a patient.

At times it is desirable to deliver to a patient multiple solutions or medications including a primary solution and a secondary solution. In such circumstances, IV bags containing the primary solution and the secondary ("piggyback") solution may be joined with a Y-connector and a tube from the Y-connector connected to an infusion pump. The infusion pump may include, for example, a peristaltic pump element controllably pumping the solution to the patient as well as pressure sensors for sensing occlusion and the like as well as air-in-line sensors such as may detect bubbles in the fluid.

Preferential delivery of the piggyback solution may be obtained by elevating the IV bag containing the piggyback solution above that which contains the primary solution. The infusion pump will pump material from the bag at the higher elevation.

SUMMARY OF THE INVENTION

The present inventor has recognized a number of problems that can occur when administering multiple fluids using an IV pump as described above. First, at some pump rates, solution may be pulled both from the primary and secondary IV bags despite the higher elevation of the secondary bag. Second, in the event of an infusion pump failure, gravity feeding of the materials from the primary and secondary bag may occur at a higher than desired flow rate.

The present invention addresses these problems by providing a line management apparatus connectable to a primary and secondary IV bag for monitoring flow rate and independently controlling flow through the separate tubes leading to each of the primary and secondary IV bags. By monitoring flow and pinching off one of the tubes, a switchover between bags may occur only after the secondary bag is depleted as sensed by flow. Flow monitoring also allows detection of an infusion pump failure and controlling the flow rate independently of the infusion pump. In this regard, the present invention can also be used as a highly precision gravity flow infusion system. Finally, during switchover, a signal can be provided to the operator positively signaling the switchover has occurred, therefore providing convenience if immediately adding a different piggyback solution is desired.

Specifically then the present invention provides an IV line management apparatus for intravenous administrations of multiple solutions having a housing for receiving a piggyback tubing assembly comprising a primary IV tube from a primary IV bag as joined to a secondary IV tube from a secondary IV solution bag with a manifold connector (for example, a Y-connector or multi-way connector) and an exit tube passing from the manifold connector. First and second metering clamps engage the primary IV tube and secondary IV tube respectively when the piggyback tubing assembly is received within the housing for controlling flow through the primary IV tube and secondary IV tube according to electrical signals received by the first and second metering clamps, and at least one flow rate sensor senses flow through the tubing assembly. A controller comprising an electronic computer executing a stored program receives at least one signal from at least one flow rate sensor and provides electrical signals to the first and second metering clamps according to the stored program.

It is thus a feature of at least one embodiment of the invention to provide superior management of piggyback IV administration by allowing independent control of the streams from two IV bags.

The electronic computer may execute the stored program to control the first or second metering clamps to limit flow through the flow rate sensor to a predetermined maximum value.

It is thus a feature of at least one embodiment of the invention to provide a backup for limiting fluid flow in the event of an infusion pump failure.

The electronic computer may execute the stored program to provide electrical signals to the first and second electrical metering clamps in a first state to stop flow through the primary IV tube while allowing flow through the secondary IV tube until a flow rate lower than a second predetermined value is detected, and then to provide electrical signals to the first and second electrical metering clamps in a second state to stop flow through the secondary IV tube while allowing flow through the primary IV tube.

It is thus a feature of at least one embodiment of the invention to provide for automatic switchover between solution bags preventing flow from both bags simultaneously.

The IV line management apparatus may further include an alarm annunciator for indicating a transition between the first and second states.

It is thus a feature of at least one embodiment of the invention to positively signal a depletion of the secondary solution.

The first and second metering clamps may provide opposed jaws fitting about the primary IV tubing and secondary IV tubing and the electrical signals to the first and second metering clamps may control a separation of the jaws in pinching off the primary IV tubing or the secondary IV tubing.

It is thus a feature of at least one embodiment of the invention to provide a system for controlling fluid flow in separate IV lines that maintains a sterile envelope around the IV solution.

The electrical signals to the first and second metering clamps may control a separation of the jaws in pinching off the primary IV tubing or the secondary IV tubing to multiple different separations within a range of separations to provide control between a fully open and fully closed separation.

It is thus a feature of at least one embodiment of the invention to provide the ability to meter fluid as well as to shut fluid flow off.

The IV line management apparatus may include electrical switch operators positioned on the housing near the primary IV tubing and secondary IV tubing wherein the controller executes a stored program to respond to an operator actuation of a switch operator near one of the primary IV tubing and secondary IV tubing to cause a pinching off of alternate ones of the primary and secondary IV tubes depending on the operator actuated.

It is thus a feature of at least one embodiment of the invention to provide a simple method of designating a source of fluid flow.

The IV line management apparatus may include display elements positioned on the housing near the primary IV tubing and secondary IV tubing and communicating with the controller to indicate a state of flow through the primary IV tubing and secondary IV tubing.

It is thus a feature of at least one embodiment of the invention to provide a simple method of monitoring two different fluid flows.

The IV line management apparatus may include display elements that may be colored lights indicating a state of flow as one of open, closed, or metered and further may provide the colors and organization of a standard traffic light.

It is thus a feature of at least one embodiment of the invention to provide a simple intuitive display of multiple states of flow for different IV lines.

The IV line management apparatus may further include additional sensors sensing solution in the primary and secondary IV tubing, the sensors selected from the group consisting of air-in-line sensors, pressure sensors, and tubing-in-place sensors.

It is thus a feature of at least one embodiment of the invention to permit the line management apparatus to be used as a precise gravity feed IV system without an infusion pump.

One embodiment of the flow rate sensor is infrared sensor sensing drips passing through a drip chamber.

It is thus a feature of at least one embodiment of the invention to permit use with a variety of flow sensing techniques.

The housing may include a cover closing over the piggyback tubing assembly when received within the housing to retain the tubing within the housing.

It is thus a feature of at least one embodiment of the invention to provide a positive retention of the piggyback tubing assembly that preserves its integrity and engagement in the housing.

The cover may include a window positioned to allow visual inspection of the tubing.

It is thus a feature of at least one embodiment of the invention to provide the ability to continuously visually monitor the piggyback tubing assembly.

The IV line management apparatus may further include a lock for holding the cover closed against the housing.

It is thus a feature of at least one embodiment of the invention to permit a tamperproof control of multiple IV lines.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

DETAILED DESCRIPTION OF THE PREFERRED EMBODIMENT

Figure 1:
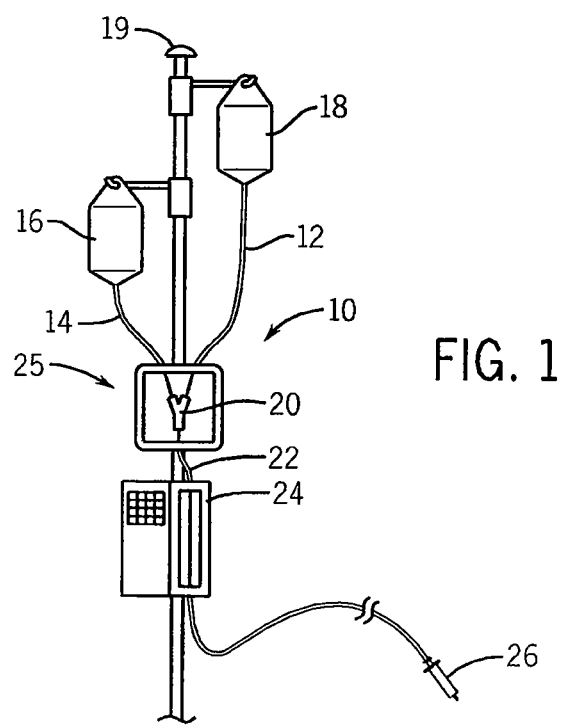
FIG. 1 is a simplified perspective representation of an example line management apparatus per the present invention used in conjunction with a piggyback tubing assembly and an infusion pump.

Referring now to FIG. 1, a line management apparatus 10 of the present invention may receive IV lines 12 and 14 from a primary IV bag 16 and a secondary ("piggyback") IV bag 18 through a top surface of the line management apparatus 10. Generally the secondary IV bag 18 may be mounted higher than the primary IV bag 16 on an IV pole 19; however, this is not required in the present invention. The IV lines 12 and 14 may be joined by a Y-connector 20 leading to an outlet line 22, the latter of which may be received by a standard infusion pump 24. Generally the IV lines 12 and 14, Y-connector 20, and outlet line 22 provide a piggyback tubing assembly 25.

The infusion pump 24, as is understood in the art, provides a peristaltic pump element that accurately meters liquid through the outlet line 22 and to a needle 26 or the like that may be inserted into a patient (not shown). As is understood in the art, the infusion pump 24 may further provide sensors such as air-in-line sensors and pressure sensors for monitoring the flow through outlet line 22 and a tubing in-place sensor for ensuring the tubing of outlet line 22 is properly seated in the pump 24. The infusion pump 24 may further provide for a time control of the flow through outlet line 22 as well as alarms indicating problems with that flow.

Figure 2:
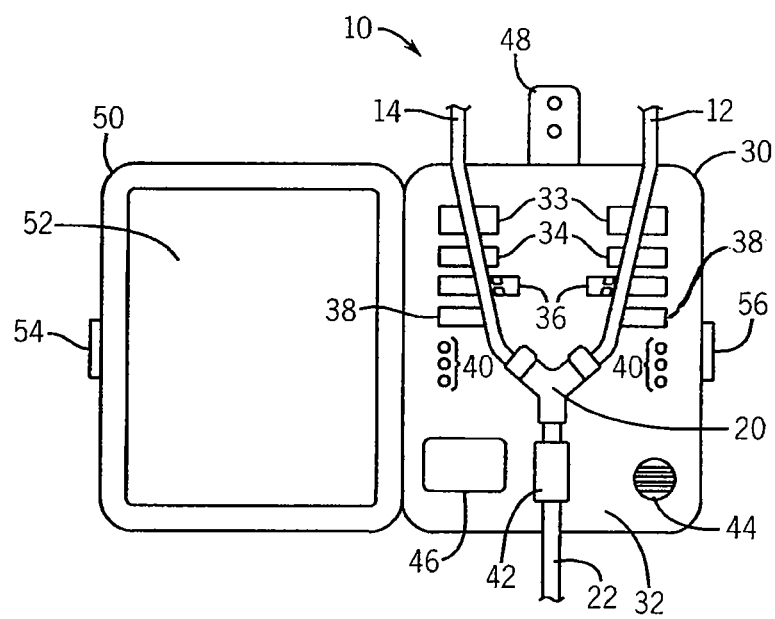
FIG. 2 is a front elevational view of the line management apparatus of the present invention with the cover open showing various sensors, actuators, displays and annunciators.

Referring now to FIG. 2, the line management apparatus 10 may provide for a housing 30 having a front face 32 that may receive the piggyback tubing assembly 25 within channels and sockets in the front face 32. In particular, each of the IV lines 12 and 14 may pass downward through left and right air-in-line sensors 33, left and right tubing loaded sensors 34, and left and right metering clamps 36.

The air-in-line sensors 33 may consist of two ultrasonic transducers: one serving as an actuator to convert electrical energy into mechanical energy, and the other serving as a receiver to convert mechanical energy into electrical energy. In one embodiment, the actuator is implemented with a piezoelectric actuator. When an electrical signal is applied to the piezoelectric actuator, cyclic deformation of piezoelectric material inside the actuator produces a stress wave that travels across the tubing of IV lines 12 and 14. Due to the significant difference of attenuation factor from liquid to air, the stress wave detected by the receiver varies significantly depending upon whether liquid or air is within the tubing adjacent to the receiver. Therefore, air can be differentiated from liquid, and an indication of the presence of air bubbles or line empty state may be made.

The tubing-loaded sensors 34 detect the presence of tubing of IV lines 12 and 14 and outlet line 22 properly seated in the channels in the housing 30. The seated tubing can be with or without liquid in it. In one embodiment, the tubing-loaded sensors 34 consist of a magnet and a Hall sensor. When tubing is loaded, the magnet is pushed closer or father away from the Hall sensor, depending upon the chosen implementation. Therefore, the signal obtained from the Hall sensor can be used to determine whether the tubing is loaded. In another embodiment, the tubing-loaded confirmation sensor consists of a LVDT (Linear Variable Displacement Transducer). When a tube is loaded, movement of the ferromagnetic core results in a transducer voltage change due to mutual inductance change. The resulting voltage is used to determine the tubing loading condition. In another embodiment, the tubing loading condition can be determined by analyzing a signal from the air-in-line sensor 33 receiver due to observable differences among tube not loaded, empty tube, and liquid filled tube states.

An upstream occlusion condition can also be detected by the same type of sensors that detect the presence of tubing.

Positioned below the metering clamps 36 are the operators of left and right electrical switches 38, and left and right indicator banks 40, each positioned near a respective IV line 12 and 14 to be clearly associated with one of those IV lines 12 and 14. Each indicator banks 40 may comprise three LEDs providing red, yellow, and green lights and ordered from top to bottom in the manner of a standard traffic signal to accommodate a color blind user. The LEDs may indicate conditions such as liquid flowing, standby (tubing filled with liquid, but liquid is not flowing), or no flow (no tubing loaded, air in tubing, or tubing closed by flow regulator).

Outlet line 22 leading from the Y-connector 20 passes through a flow rate sensor 42 after which outlet line 22 may exit the line management apparatus 10.

The front face 32 also provides a baffle for a speaker 44. The speaker 44 can be used to generate an alarm sound when a preset condition is met, such as flow rate out of range, line empty/air in line, tube not loaded, both line switches at off position when flow is expected, as well as for other conditions that will be described below.

A screen 46 for displaying alphanumerics or text may also be provided, for example, to indicate flow rate. Line condition can also or alternatively be indicated by the screen 46 which may be provided as an LCD, LED or other commonly known type of display screen.

The housing may further provide a support tab 48 at its top edge for attachment to the IV pole 19 and may have a hinging cover 50 pivoting about one vertical edge of the housing 30 to open and close over the front face 32 of the housing 30. The cover 50 may provide for a central transparent window 52 and a lock hasp 54 engaging with a corresponding lock hasp 56 on the housing that allows locking of the cover 50 in a closed position on the housing 30. When the cover 50 is closed over the front face 32, it retains the piggyback tubing assembly 25 therein and the window 52 allows visual inspection of each of the elements on the front face 32.

Figure 3:
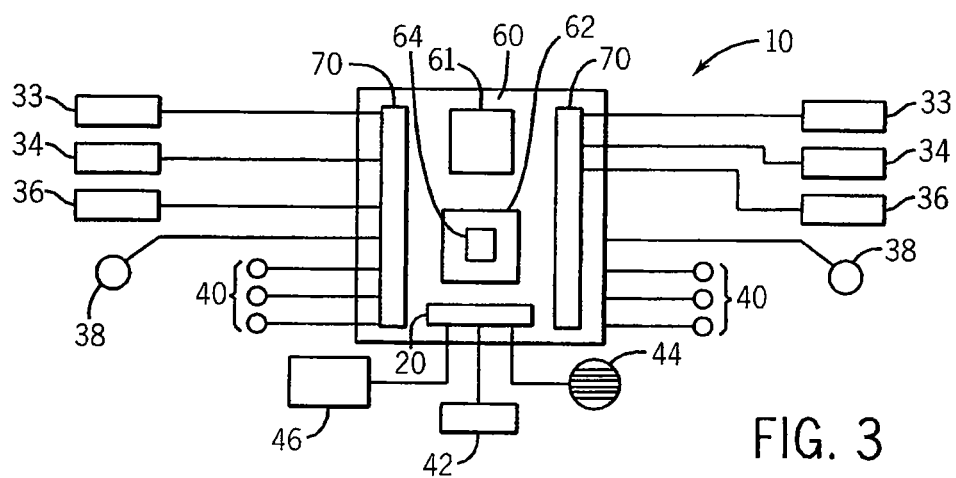
FIG. 3 is a block diagram of the principal elements of the pump including a processor for monitoring the sensors of the present invention using a stored program and for controlling actuators.

Referring now to FIG. 3, the line management apparatus 10 may include a controller 60 (which may be a processor 61 based system) having a memory 62 for holding a stored operating program and data 64 controlling operation of the line management apparatus 10 as will be described below. In particular, the controller 60 may use the data in the memory 62 to control metering clamps 36 to ensure the desired dose and delivery rate to the patient. The controller 60 may further communicate with the flow rate sensor 42 of the present invention for receiving a signal therefrom as will be described. Further, the controller 60 executing the stored program 64 may read a signal from the air-in-line sensors 33 and the tubing loaded confirmation sensors 34.

Figure 4:
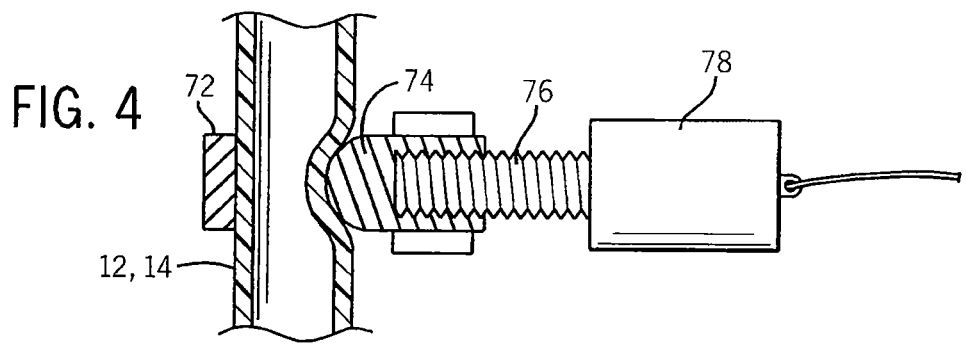
FIG. 4 is a cross-sectional view of metering clamp actuators showing their operation on a contained tubing element.

Referring still to FIG. 3, the controller 60 may also communicate with a screen 46 for displaying and/or inputting various programming and operating parameters, a speaker associated with speaker 44 for providing audible alarm signals, and switches 38 for inputting data to the controller 60, for example, for selecting among solution delivery through IV lines 12 and 14. The controller 60 may also provide for signals to the indicator bank 40 to control their illumination. This communication may be through standard interfaces 70 understood in the art Referring now to FIG. 4, the metering clamps 36 may provide for opposed stationary jaw 72 and movable jaw 74 that may flank each of IV lines 12 and 14. Movable jaw 74 may communicate through a lead screw 76 with a motor 78, for example a servo or stepper motor, that may rotate the lead screw 76 to move the jaws 72 and 74 to various degrees of separation. As such, the jaws 72 may close to fully block flow through the IV lines 12 and 14, or open fully for free flow through IV lines 12 and 14 or may be positioned in between open and closed to provide for a metering of flow. In an alternative embodiment, where only full or no flow is required, the metering clamps 36 may be actuated by solenoids replacing the servo or stepper motors.

Figure 5:
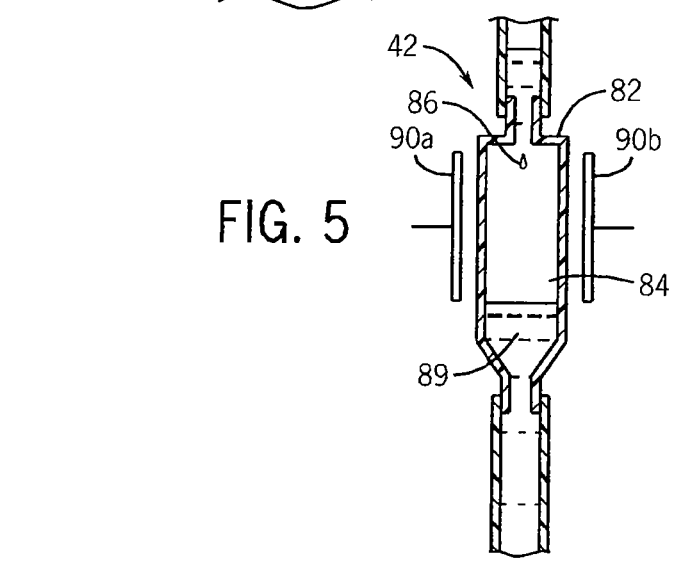
FIG. 5 is a fragmentary front elevational cross-sectional view through a flow rate sensor having a chamber providing falling drops positionable between capacitor plates flanking the flow rate sensor chamber when the flow rate sensor chamber is inserted into the pump.

Referring now to FIG. 5, in the first embodiment of the invention, the flow rate sensor 42 may provide for a generally cylindrical housing 82 receiving a flexible tube of the IV line 12 or 14 and having a diameter substantially larger than the diameter of the tube of IV lines 12 and 14. A connection between the tube and the housing 82 provides an orifice opening into an air space 84, the orifice forming liquid from the IV bag 16 or 18 into drops 86 that may fall through the air space 84 into a pool 89 at the bottom of the cylindrical housing 82. The pool 89 may communicate with a second tube providing a drain therefrom and a continuation of the IV line as outlet line 22.

When the flow rate sensor 42 (formed with the piggyback tubing assembly 25) is placed within a socket in the front face 32 of the housing 30, it will be flanked by first and second plates 90a and 90b positioned across a diameter of the cylindrical housing 82 and accordingly across the air space 84. Drops 86 passing through the air space 84 thereby create a change in capacitance between the plates 90a and 90b caused by the increased dielectric constant of the material of the drop 86. For example, the dielectric constant of water is approximately 34 to 78 times that of air. This capacitance may be measured by a number of techniques including, for example, measurement of changes in a frequency of the oscillator incorporating the capacitance between the plates 90a and 90b into a resonant circuit or by use of the capacitance between plates 90a and 90b as part of an integrator and measuring a time constant of a ramping up of the integrator after periodic reset. These fluctuations in capacitance may be used to count the drops 86 and deduce a flow rate. Alternatively an infrared light beam may be used to count drops in the situation.

Figure 6A:
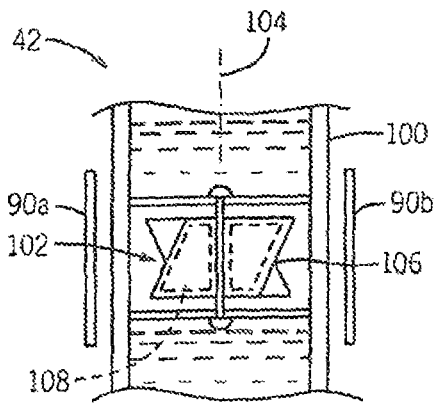
FIGS. 6a and 6b are a fragmentary front cross-sectional view and a top plan cross-sectional view, respectively, of a second embodiment of the flow rate sensor providing a chamber with a contained turbine wheel and flanking capacitive sensors when the flow rate sensor chamber is inserted into the pump.
Figure 6B:
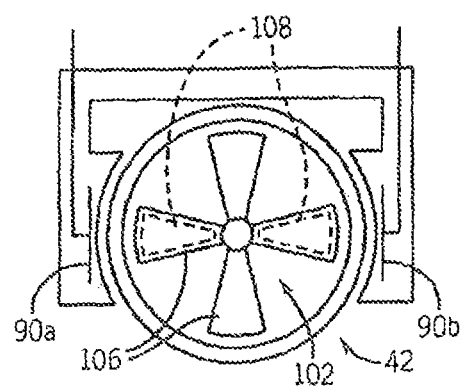

Referring now to FIGS. 6a and 6b, in a second embodiment the flow rate sensor 42 may also provide for a cylindrical housing 100. In this case the cylindrical housing 100 holds suspended therein a free spinning turbine 102 having a rotational axis 104 generally along the direction of flow and along the axis of the cylindrical housing. The cylindrical housing 100 may be attached at its upper and lower ends to outlet line 22 leading from the Y-connector 20 to be placed in series with the outlet line 22. Generally, the turbine 102 provides for one or more canted blades 106 having a known pitch to cause a predetermined rotational rate of the turbine 102 with flow of the liquid within the cylindrical housing 100 along axis 104.

Plates 90a and 90b may flank the cylindrical housing 100 when the flow rate sensor 42 is placed within the socket in the front face 32 of the housing 30 as described above with respect to the embodiment of FIG. 5. One or more blades 106 of the turbine 102 may include high conductivity or dielectric inclusions 108, for example aluminum inserts or metal plating, that change the effective spacing of the capacitor plates 90a and 90b with rotation of the turbine 102. Alternatively, the dielectric material of the turbine blade 106 may provide for the necessary variations in capacitance between the plates 90a and 90b causing a variation in capacitance as a function of rotation of the turbine 102. It will be understood that the change in capacitance signal between the plates 90a and 90b may be used to deduce rotation of the turbine 102 and thus the total flow of liquid through the outlet line 22. It will be appreciated that other sensing techniques such as Hall effect sensing may also be used.

Although two flow rate sensors have been described above, it will be appreciated that other flow rate sensors may also be used in this capacity including, for example, thermal time of flight sensors, ultrasonic sensors and the like.

For example, in another embodiment, the flow rate sensor 42 for outlet line 22 may consist of an ultrasonic flow meter and the supporting circuits. The ultrasonic flow meter may have two piezoelectric transducers and a tubing section between the two transducers. Mechanical stress waves can be generated by applying an electrical signal to either transducer. Velocity of stress wave propagation along and against the flow direction within the tube is affected by the velocity of the liquid. By knowing the cross section of the tubing section and the length of the tubing section, flow rate can be calculated using time difference between the stress wave propagation directions.

In another embodiment, the flow rate sensor 42 for the outlet line 22 may consist of a laser based flow meter and the supporting circuits. Liquid inside a tubing section with a specific cross section can be heated with a heating laser, and the change in fluid reflectivity and/or diffractivity due to added thermal energy can be utilized to measure flow rate. The change in reflectivity and/or diffractivity can be detected by a sensing laser, photo diode, and corresponding optical components such as mirrors and apertures.

In another embodiment, the flow rate sensor 42 for the outlet line 22 may consist of a thermal time-of-flight based flow meter and the supporting circuits. Fluid flowing through the tubing is heated up by a certain amount of thermal energy. A thermal probe(s) at a downstream location measures the temperature change of the fluid. The flow rate can be calculated from temperature change data.

In another embodiment, the flow rate sensor 42 for the outlet line 22 may consist of two pressure sensors and the supporting circuits. The two pressure sensors are positioned at a certain distance along the flow direction. Differential pressure can be calculated from pressure values measured by the two pressure sensors. By knowing the cross section of the tubing, distance between two differential pressure sensors, and the differential pressure, flow rate can be calculated. Any of various pressure sensors known to one skilled in the art may be employed.

In another embodiment, the flow rate sensor 42 for the outlet line 22 may be a differential pressure sensor, using a piezoresistive monolithic silicon pressure sensor and supporting circuitry. Commercially available piezoresistive sensing element (such as part #MPVZ4006G from Freescale Semiconductor, Inc) can be utilized to sense the differential pressure at two different locations along the flow direction. Deformation of the diaphragm results in resistance change, which can be used to directly calculate the differential pressure. Once differential pressure is obtained, with known cross section of tubing and distance between two pressure ports along the line, flow rate can be measured.

Figure 7:
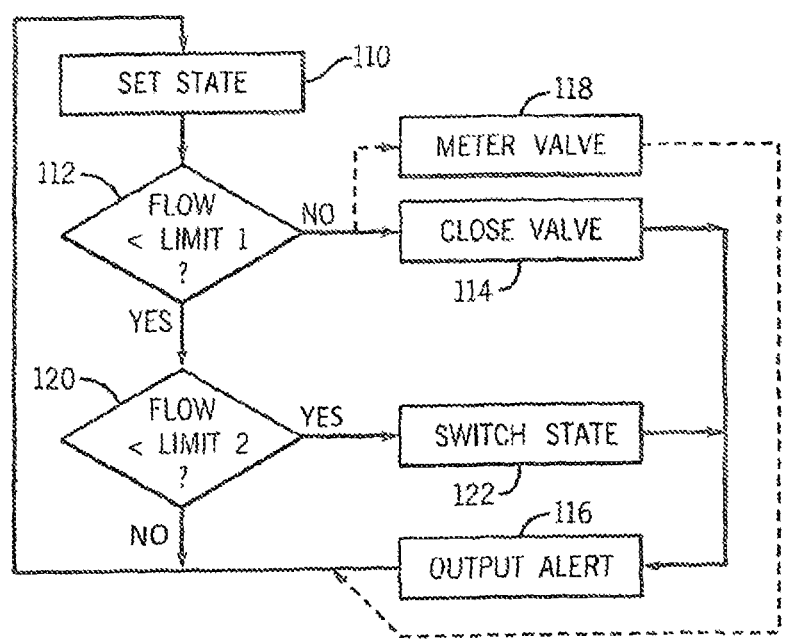
FIG. 7 is a simplified flowchart of a program executing on the processor FIG. 3.

Referring now to FIGS. 1, 3 and 7, the program 64 executed by the processor 61, as indicated by process block 110, may receive a state setting by the user indicating in which of IV lines 12 and 14 initial flow is desired. The state setting signal may come from switches 38 which when pressed indicate that the IV line 12 or 14 closest to the switch 38 is to be the line that will have flow and the remaining line will be clamped off for no flow by adjustment of the appropriate metering clamps 36. At this time, indicator bank 40 shows a green light if flow is occurring in the particular tube and a red light if no flowing is occurring.

As indicated by decision block 112, as material flows through outlet line 22, the flow is monitored by flow rate sensor 42 to make sure it is below a predetermined limit that should be provided to the patient. This first predetermined limit enforces a degree of safety in the event that the infusion pump 24 fails in an open state or may be a routine monitoring used when the line management apparatus 10 is used without an infusion pump 24.

If the flow exceeds the indicated limit, then the processor 61 may close the metering clamp 36 associated with the active IV line 12 or 14 as indicated by process block 114 and provide an output alarm as indicated by process block 116. The alarm will typically be an audible alarm demanding immediate attention.

When the line management apparatus 10 is being used without an infusion pump 24, then instead, at process block 118, the metering clamp 36 associated with the open IV line 12 and 14 may be tightened down until proper flow rate is obtained. This metering is indicated by a green or yellow illumination in the corresponding indicator bank 40 and provides closed loop regulation of flow in conjunction with flow rate sensor 42.

If the first predetermined flow rate limit has not been exceeded at decision block 112, then at decision block 120 it is determined whether the active IV line 12 or 14 has a flow below a second predetermined limit indicating depletion of the solution in the associated IV bag 18 or 16. If this second predetermined flow limit is not maintained, then the program 64 moves to process block 122 and a state-switch occurs in which the open IV line 12 or 14 is fully closed (typically the IV line 12 associated with the piggyback solution) and the other IV line 12 or 14 (typically the primary IV line 14) is opened. In this case a visual alarm may be output indicating to a healthcare professional that the secondary solution from IV bag 18 has been exhausted.

Figure 8:
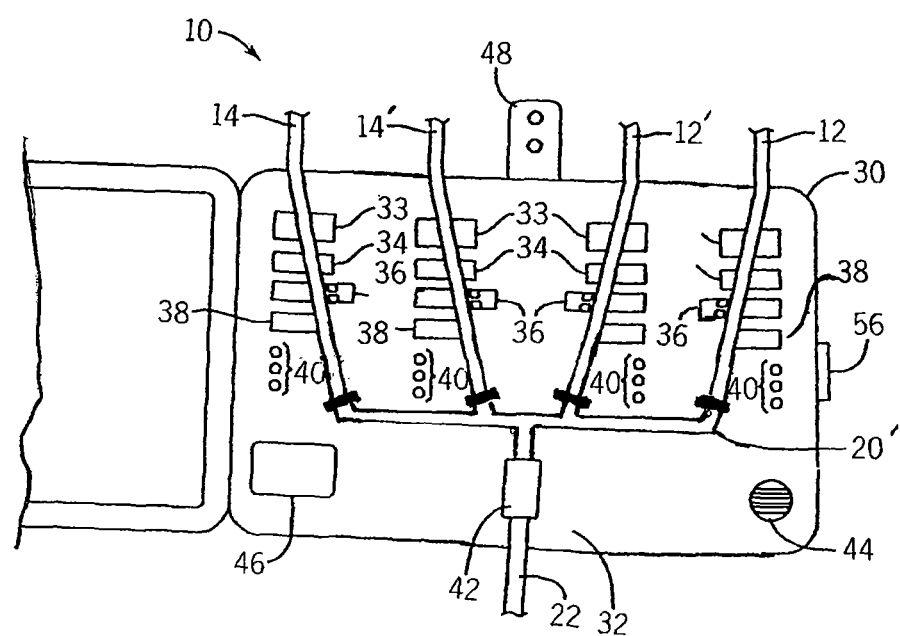
FIG. 8 is a figure similar to FIG. 2 showing an embodiment using a multi-way connection system.

Referring now to FIG. 8, it will be appreciated that the principles of the present invention, as described above, may be extended to a system having additional inlet IV lines beyond primary IV line 12 and secondary IV line 14, for example, to provide for a tertiary IV line 12', and optionally a quaternary IV line 14' and possibly additional IV lines joined by a manifold connector 20' merging the flows from these multiple inlet IV lines into the single outlet line 22. In this case the air-in-line sensors 33, tubing loaded sensors 34, metering clamps 36, switches 38 and indicator banks 40 may be duplicated for each of these inlet IV lines to provide independent sensing and control of each line.

Such multi-way systems may be desirable for anesthesiology where additional medications and materials need to be simultaneously administered in a controlled fashion to a patient. Such multi-way systems may also be desirable for staging multiple bags of medications for sequential delivery and may operate, for example, to allow the flow through one inlet IV line at a time until a flow rate drop below a predetermined amount, and then to switch to the next IV line in a predetermined sequence. Generally, it is contemplated that the invention may provide for a wide range of different inlet IV line numbers ranging from 2 to 8 and thus including two inlet IV lines, greater than two inlet IV lines, greater than three inlet IV lines, etc. The extension of the circuitry of FIG. 3 to include additional control lines will be understood from this disclosure to those of ordinary skill in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. An IV line management apparatus for intravenous administrations of multiple solutions using an infusion pump comprising:

a housing for receiving a piggyback tubing assembly comprising a primary IV tube from a primary IV solution bag as joined to a secondary IV tube from a secondary IV solution bag with a joining-connector and an exit tube passing from the joining-connector;

first and second metering clamps engaging the primary IV tube and the secondary IV tube respectively when the piggyback tubing assembly is received within the housing for controlling flow through the primary IV tube and the secondary IV tube according to electrical signals received by the first and second metering clamps;

at least one flow rate sensor sensing flow through the piggyback tubing assembly and delivering at least one signal indicating a flow rate; and a controller comprising an electronic computer executing a stored program and receiving the at least one signal indicating the flow rate from the at least one flow rate sensor and providing the electrical signals based upon the flow rate to the first and second metering clamps according to the stored program;

wherein the electronic computer executes the stored program to provide the electrical signals based upon the flow rate to the first and second metering clamps to stop flow through the primary IV tube while allowing flow through the secondary IV tube until a flow rate lower than a second predetermined value is detected indicating an exhaustion of the secondary IV solution bag and then to provide the electrical signals based upon the flow rate to the first and second metering clamps to stop flow through the secondary IV tube while allowing flow through the primary IV tube; and wherein the electronic computer executes the stored program to provide the electrical signals based upon the flow rate to the first and second metering clamps to allow flow through one of the primary IV tube and the secondary IV tube until a flow rate greater than a first predetermined value is detected indicating a failure of the infusion pump and then to provide the electrical signals based upon the flow rate to the first and second metering clamps to stop flow through the one of the primary IV tube and the secondary IV tube.

2. The IV line management apparatus of claim 1 wherein the electronic computer executes the stored program to control the first or second metering clamps to limit flow through the at least one flow rate sensor to a predetermined maximum value.

3. The IV line management apparatus of claim 1 further including an alarm enunciator for indicating a transition between stopping flow through the primary IV tube and allowing flow through the secondary IV tube, and stopping flow through the secondary IV tube and allowing flow through the primary IV tube or between allowing flow through one of the primary IV tube and the secondary IV tube, and stopping flow through the one of the primary IV tube and the secondary IV tube.

4. The IV line management apparatus of claim 1 wherein the first and second metering clamps provide opposed jaws fitting about the primary IV tube and the secondary IV tube and wherein the electrical signals to the first and second metering clamps control a separation of the jaws in pinching off the primary IV tube or the secondary IV tube.

5. The IV line management apparatus of claim 4 wherein the electrical signals to the first and second metering clamps control the separation of the jaws in pinching off the primary IV tube or the secondary IV tube to multiple different separations within a range of separations to provide control between a fully open and a fully closed separation.

6. The IV line management apparatus of claim 1 further including an electrical switch operator positioned on the housing near the primary IV tube and the secondary IV tube and wherein the controller executes the stored program to respond to an operator actuation of the switch operator near one of the primary IV tube and the secondary IV tube to cause a pinching off of alternate ones of the primary IV and the secondary IV tubes depending on the operator actuated.

7. The IV line management apparatus of claim 1 further including display elements positioned on the housing near the primary IV tube and the secondary IV tube and communicating with the controller to indicate a state of flow through the primary IV tube and the secondary IV tube.

8. The IV line management apparatus of claim 7 wherein the display elements may be lamps of different colors indicating the state of flow as one of: open, closed, and metered between open and closed.

9. The IV line management apparatus of claim 8 wherein the lamps provide the colors and, organization of a standard traffic light.

10. The IV line management apparatus of claim 1 wherein the housing further includes additional sensors sensing the solutions in the primary IV and the secondary IV tubes, the sensors selected from the group consisting of: air-in-line sensors, pressure sensors, and tubing-in-place sensors.

11. The IV line management apparatus of claim 1 wherein the at least one flow rate sensor is selected from the group consisting of a drip chamber, a turbine, and a thermal time-of-flight sensor.

12. The IV line management apparatus of claim 1 wherein the housing includes a cover closing over the piggyback tubing assembly when received within the housing to retain the tubes within the housing.

13. The IV line management apparatus of claim 12 wherein the cover includes a window positioned to allow visual inspection of the tubes.

14. The IV line management apparatus of claim 13 further including a lock for holding the cover closed against the housing.

15. The IV line management apparatus of claim 1 wherein the joining-connector is a Y-connector.

16. An IV line management apparatus for intravenous administrations of multiple solutions using an infusion pump comprising:
a housing for receiving a tubing assembly comprising a primary IV tube from a primary IV solution bag as joined to a secondary IV tube from a secondary IV solution bag as joined by a multi-way connector leading to an exit tube passing from the multi-way connector;
first and second metering clamps engaging the primary IV tube and the secondary IV tube respectively when the tubing assembly is received within the housing for controlling flow through the primary IV tube and the secondary IV tube independent from one another according to electrical signals received by the first and second metering clamps;
at least one flow rate sensor sensing flow through the tubing assembly and delivering at least one signal indicating a flow rate; and
a controller comprising an electronic computer executing a stored program and receiving the at least one signal from the at least one flow rate sensor indicating the flow rate and providing the electrical signals based upon the flow rate to the first and second metering clamps according to the stored program;
wherein the electronic computer executes the stored program to provide the electrical signals based upon the flow rate to the first and second metering clamps to stop flow through the primary IV tube while allowing flow through the secondary IV tube until a flow rate lower than a second predetermined value is detected indicating an exhaustion of the secondary IV solution bag and then to provide the electrical signals based upon the flow rate to the first and second metering clamps to stop flow through the secondary IV tube while allowing flow through the primary IV tube;
wherein the electronic computer executes the stored program to provide the electrical signals based upon the flow rate to the first and second metering clamps to allow flow through one of the primary IV tube and the secondary IV tube until a flow rate greater than a first predetermined value is detected indicating a failure of the infusion pump and then to provide the electrical signals based upon the flow rate to the first and second metering clamps to stop flow through the one of the primary IV tube and the secondary IV tube; and
wherein the metering clamps control the flow between a fully blocked and a fully open flow through the one of the primary IV tube and the secondary IV tube.

17. An IV line management apparatus for intravenous administrations of multiple solutions comprising:
a housing for receiving a piggyback tubing assembly comprising a primary IV tube from a primary IV solution bag as joined to a secondary IV tube from a secondary IV solution bag with a joining-connector and an exit tube passing from the joining-connector;
first and second metering clamps engaging the primary IV tube and the secondary IV tube respectively when the piggyback tubing assembly is received within the housing for controlling flow through the primary IV tube and the secondary IV tube according to electrical signals received by the first and second metering clamps;
at least one flow rate sensor sensing flow through the piggyback tubing assembly and delivering at least one signal indicating a flow rate;
a controller comprising an electronic computer executing a stored program and receiving the at least one signal from the at least one flow rate sensor indicating the flow rate and providing the electrical signals based upon the flow rate to the first and second metering clamps according to the stored program; and
an infusion pump located downstream from the exit tube;
wherein the electronic computer executes the stored program to provide the electrical signals based upon the flow rate to the first and second metering clamps to stop flow through the primary IV tube while allowing flow through the secondary IV tube until a flow rate lower than a second predetermined value is detected indicating an exhaustion of the secondary IV solution bag and then to provide the electrical signals based upon the flow rate to the first and second metering clamps to stop flow through the secondary IV tube while allowing flow through the primary IV tube; and wherein the electronic computer executes the stored program to provide the electrical signals based upon the flow rate to the first and second metering clamps to allow flow through one of the primary IV tube and the secondary IV tube until a flow rate greater than a first predetermined value is detected indicating a failure of the infusion pump and then to provide the electrical signals based upon the flow rate to the first and second metering clamps to stop flow through the one of the primary IV tube and the secondary IV tube.

* * * * *